United States Patent
Stefanov et al.

(10) Patent No.: US 10,632,248 B2
(45) Date of Patent: Apr. 28, 2020

(54) MEDICAMENT DELIVERY DEVICE

(71) Applicant: SHL Medical AG, Zug (CH)

(72) Inventors: Slobodan Stefanov, Deerfield Beach, FL (US); Daniel Scott, Deerfield Beach, FL (US); Johnathan Weiss, Pompano Beach, FL (US)

(73) Assignee: SHL Medical AG, Zug (CH)

( * ) Notice: Subject to any disclaimer, the term of this patent is extended or adjusted under 35 U.S.C. 154(b) by 56 days.

(21) Appl. No.: 15/753,463

(22) PCT Filed: Aug. 16, 2016

(86) PCT No.: PCT/EP2016/069385
§ 371 (c)(1),
(2) Date: Feb. 19, 2018

(87) PCT Pub. No.: WO2017/041996
PCT Pub. Date: Mar. 16, 2017

(65) Prior Publication Data
US 2018/0236163 A1 Aug. 23, 2018

(30) Foreign Application Priority Data
Sep. 7, 2015 (SE) ...................................... 1551141

(51) Int. Cl.
*A61M 5/142* (2006.01)
*A61M 5/145* (2006.01)
*A61M 5/315* (2006.01)

(52) U.S. Cl.
CPC ...... *A61M 5/14248* (2013.01); *A61M 5/1452* (2013.01); *A61M 5/14244* (2013.01);
(Continued)

(58) Field of Classification Search
CPC .......... A61M 5/14248; A61M 5/14244; A61M 5/1452; A61M 2005/14256;
(Continued)

(56) References Cited

U.S. PATENT DOCUMENTS 2,605,766 A   8/1952  Uytenbogaart
3,367,199 A * 2/1968  Dankowski ............. F16H 55/42
                                              474/199

(Continued)

FOREIGN PATENT DOCUMENTS

CN        1747683 A      3/2006
CN     203724564 U      7/2014
(Continued)

OTHER PUBLICATIONS

English Translation of Abstract of Taiwanese Patent Application No. 201526938 dated Feb. 8, 2019.
(Continued)

*Primary Examiner* — Kami A Bosworth
*Assistant Examiner* — Antarius S Daniel
(74) *Attorney, Agent, or Firm* — McDonnell Boehnen Hulbert & Berghoff LLP

(57) ABSTRACT

Examples include a medicament delivery device including a housing, a medicament delivery member assembly configured to be moved from an initial position to a penetration position and from the penetration position back to the initial position, a penetration and withdrawal mechanism, an activation mechanism, and a stop mechanism, where the penetration and withdrawal mechanism includes a driver operably connected to the medicament delivery member assembly and to the activation and stop mechanism, a drive element operably connected to the driver, a biased force element connected to the drive element, and a switching element arranged between the driver and the drive element,
(Continued)

where operation of the stop mechanism allows the biased force element to interact with the drive element, causing movement of the switching element such that the driver is moved in an opposite direction and moves the medicament delivery member assembly back to the initial position.

21 Claims, 17 Drawing Sheets

(52) U.S. Cl.
CPC .............. *A61M 2005/14256* (2013.01); *A61M 2005/31516* (2013.01)

(58) Field of Classification Search
CPC ......... A61M 2005/31516; A61M 2005/14252; A61M 2005/14506; A61M 2005/2026; A61M 2005/206; A61M 5/3232; A61M 5/3287; A61M 2005/1585
See application file for complete search history.

(56) References Cited

U.S. PATENT DOCUMENTS

| | | | |
|---|---|---|---|
| 9,943,643 B2 | 4/2018 | Constantineau et al. | |
| 10,159,802 B2 | 12/2018 | Olson | |
| 2004/0010207 A1 | 1/2004 | Flaherty et al. | |
| 2010/0324485 A1 | 12/2010 | Cowe | |
| 2011/0166512 A1* | 7/2011 | Both | A61M 5/14248 604/67 |
| 2012/0172804 A1* | 7/2012 | Plumptre | A61M 5/14244 604/154 |
| 2013/0060233 A1* | 3/2013 | O'Connor | A61M 5/158 604/506 |
| 2015/0126926 A1* | 5/2015 | Giambattista | A61M 5/1454 604/135 |

FOREIGN PATENT DOCUMENTS

| | | | | |
|---|---|---|---|---|
| EP | 1326659 B1 | 12/2005 | | |
| TW | 201524544 A | 7/2015 | | |
| TW | 201526938 A | 7/2015 | | |
| WO | 2009098502 A2 | 8/2009 | | |
| WO | 2010112377 A1 | 10/2010 | | |
| WO | 2012134589 A1 | 10/2012 | | |
| WO | 2013153041 A2 | 10/2013 | | |
| WO | 2015032741 A1 | 3/2015 | | |
| WO | WO-2015032747 A1 * | 3/2015 | .......... A61M 5/3287 |
| WO | 2016074850 A1 | 5/2016 | | |

OTHER PUBLICATIONS

Search Report issued in Swedish Patent Application No. 1551141-3 dated Mar. 14, 2016.

Search Report issued in Taiwanese Patent Application No. 105127096 dated Aug. 24, 2017.

* cited by examiner

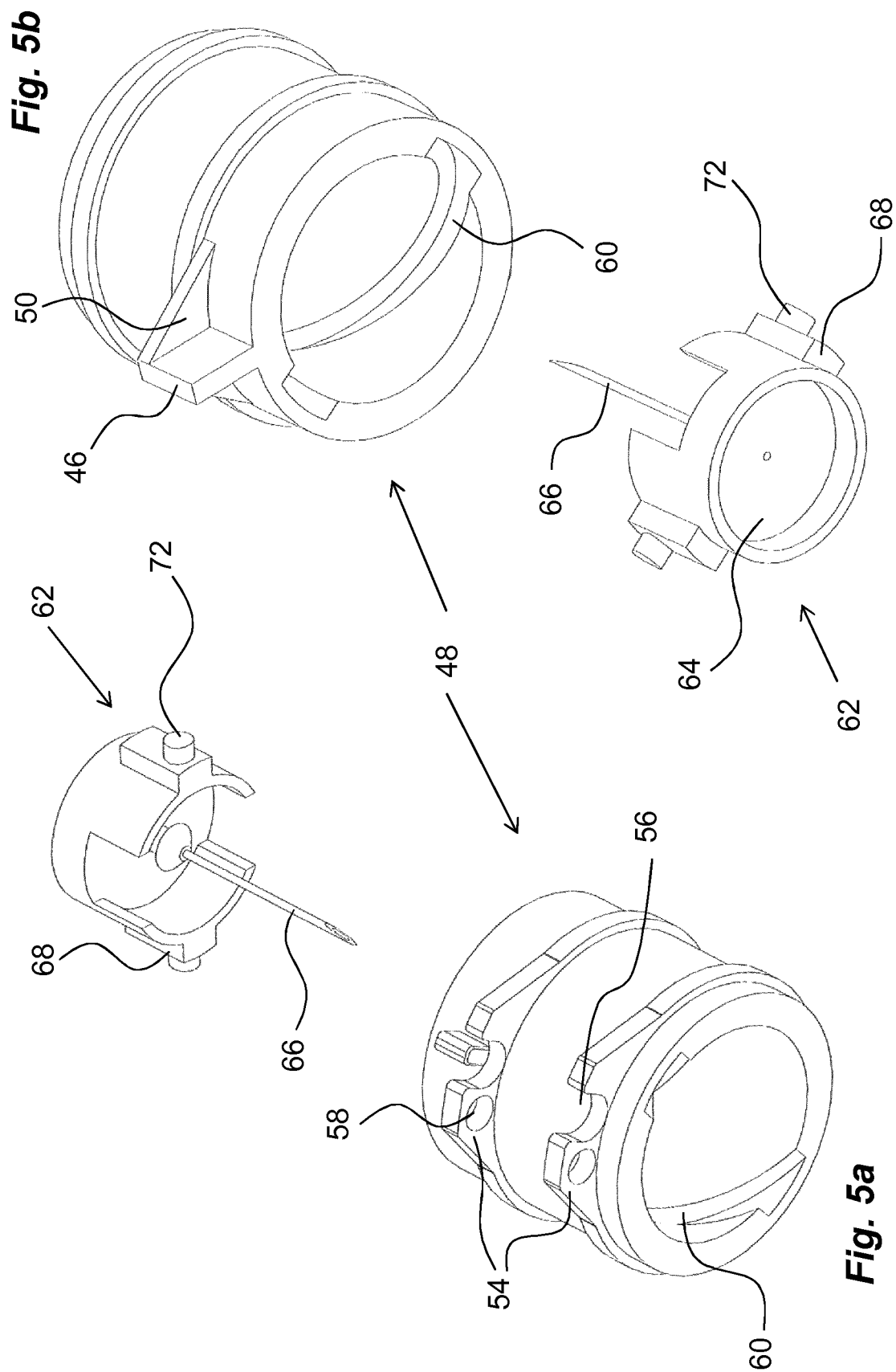

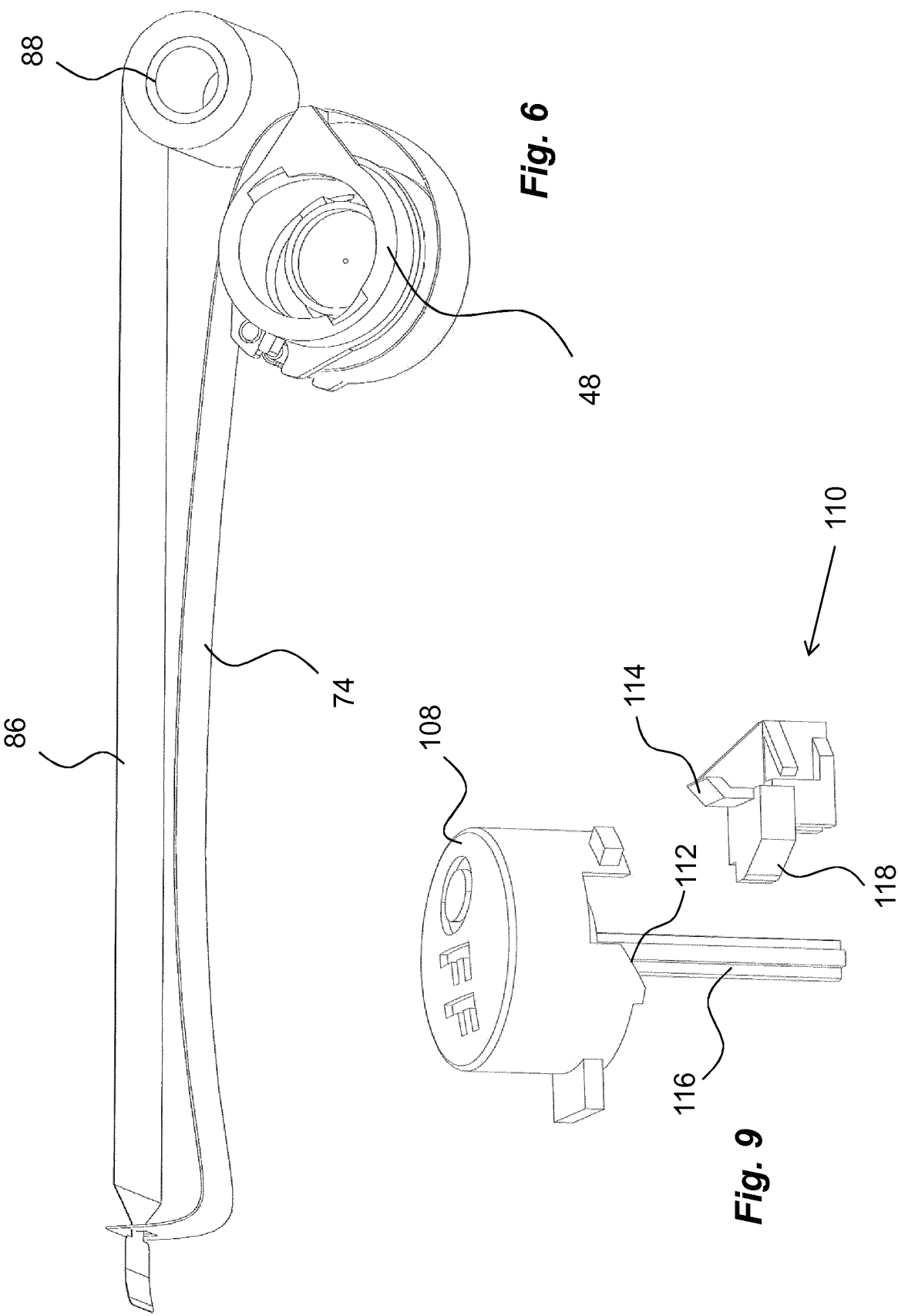

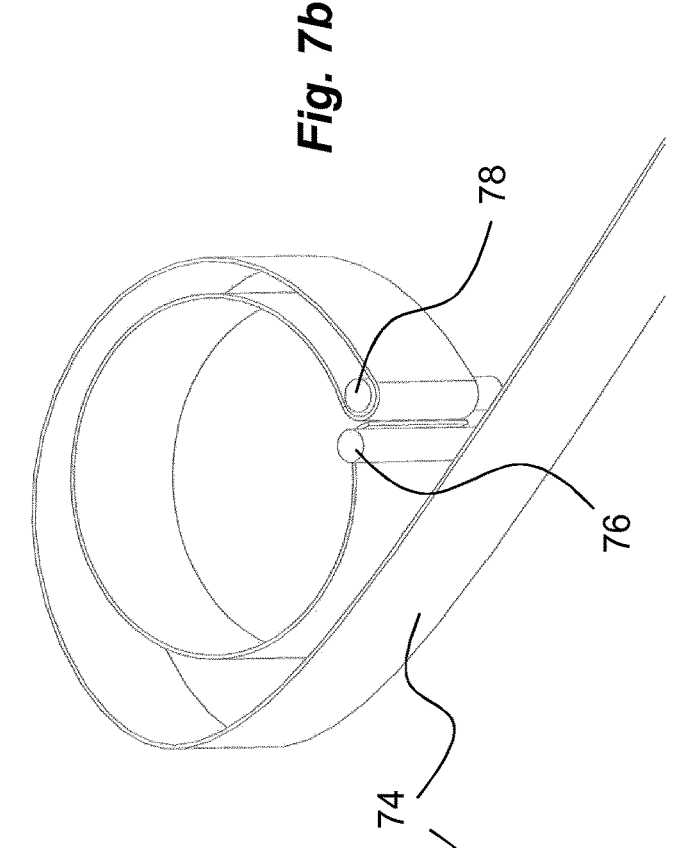
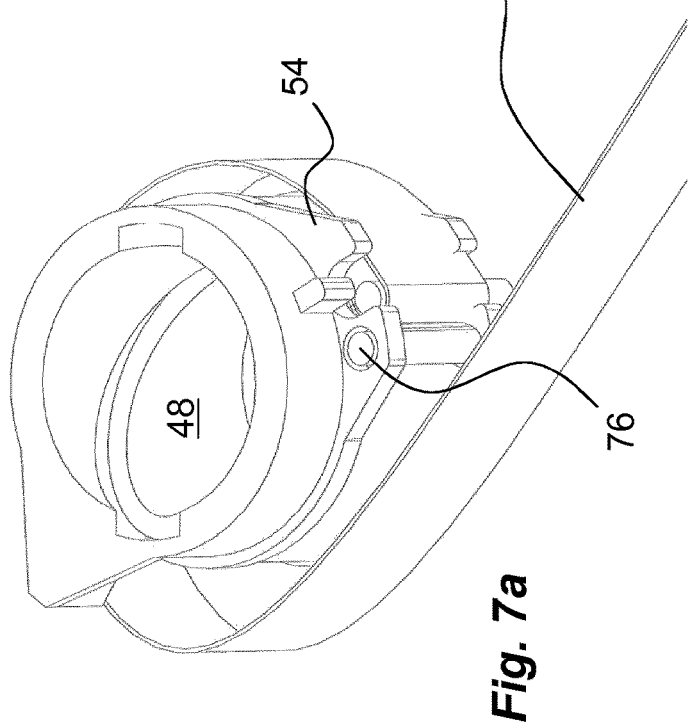
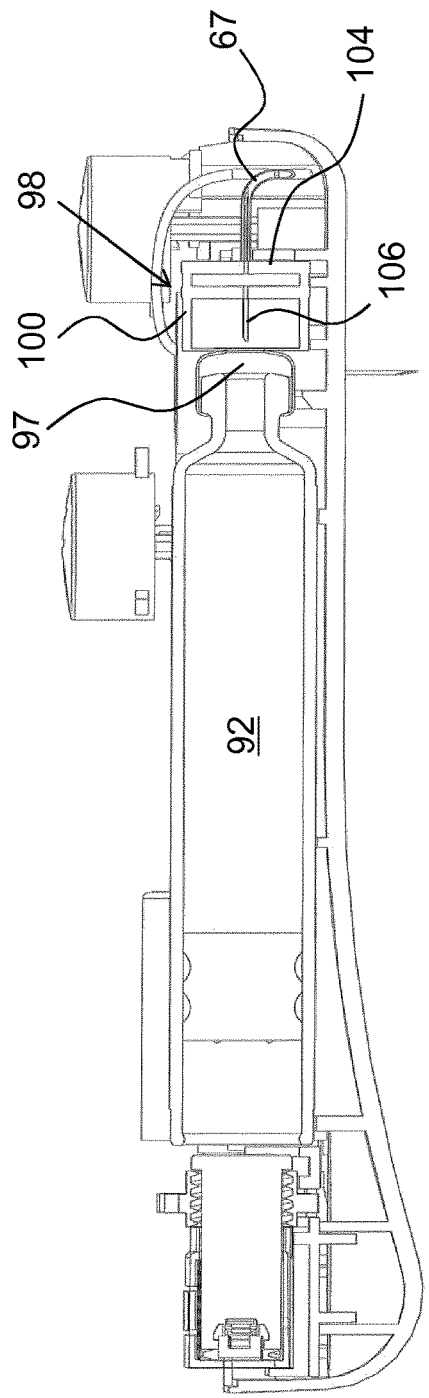
Fig. 7a
Fig. 7b
Fig. 8

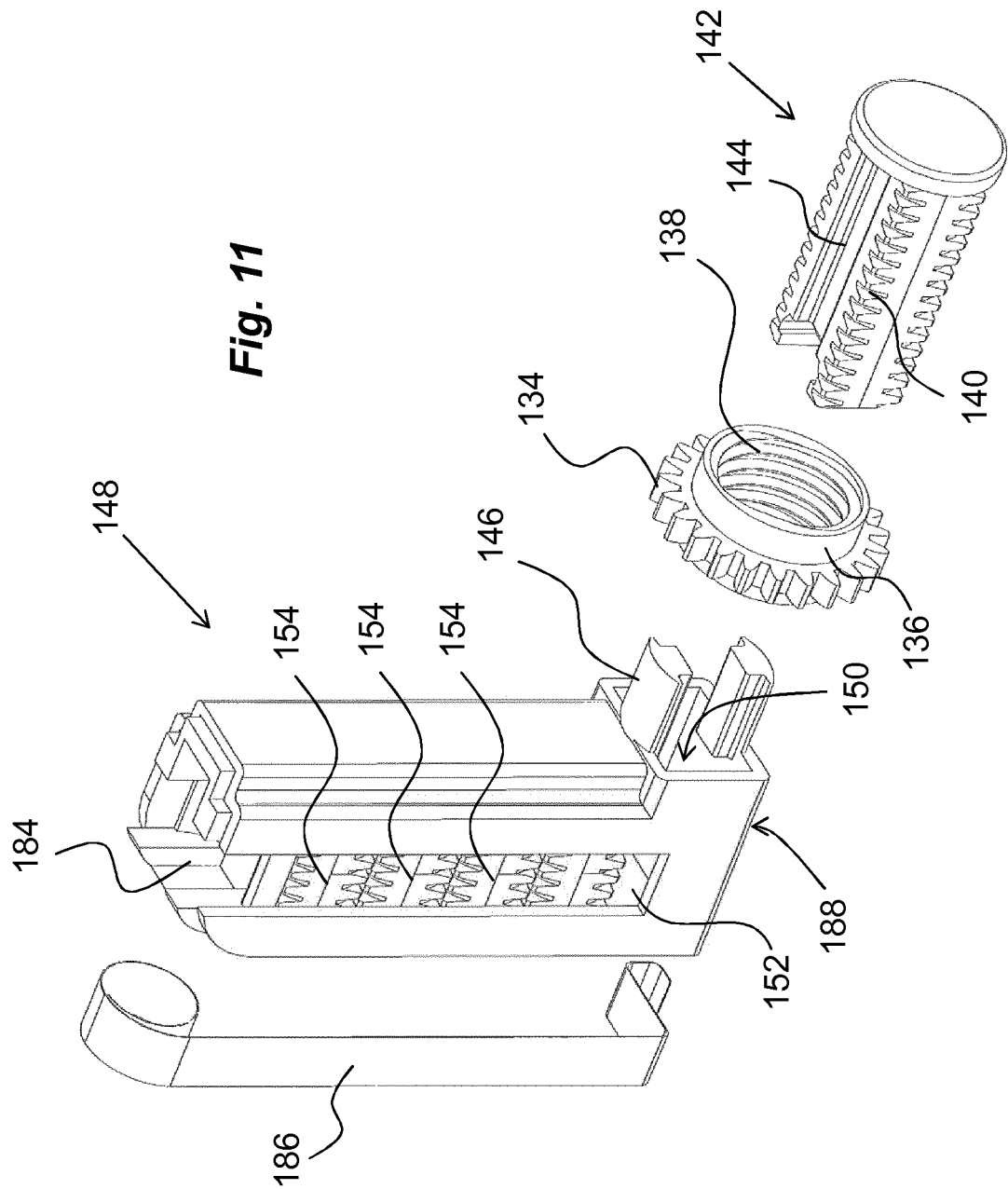

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/069385 filed Aug. 16, 2016, which claims priority to Swedish Patent Application No. 1551141-3 filed Sep. 7, 2015. The entire disclosure contents of these applications are hereby incorporated by reference into the present application.

TECHNICAL AREA

The present invention relates to a medicament delivery device and in particular to a device of limited size, capable of accurately controlling a number of functions of a medicament delivery device.

BACKGROUND OF INVENTION

For a number of years, infusers have been used that provide the patient or user with the means for administering a drug in an easy way without requiring a medically trained person, such as a physician or a nurse, to handle the device.

In order to reduce the size of the infuser, a number of alternative designs regarding the plunger rod have been developed, in particular since the plunger rod conventionally is an elongated rod having a length that enables it to empty a tubular medicament container. Document EP 1 326 659 discloses an injecting device having a flexible plunger rod bendable around a guiding wheel. The plunger rod is driven by an electric motor, via a transmission, to empty a medicament container. The drawback with the solution according to EP 1 326 659 is that the guiding wheel is rather large and is positioned behind the medicament container, as seen in a longitudinal direction, making the device unnecessary long.

Document WO 2010/112377 discloses a reusable medicament delivery device. In order to reduce the length of the device, the plunger rod is arranged in two telescopically arranged parts. The telescopic action requires two compression springs, rendering the device rather long. The device is further arranged with an electric motor. The motor, operably connected to an elongate member, is arranged to control the dose delivery movement of the plunger rods. Further, the motor is also used for retracting the plunger rods after completed dose delivery in order to be able to replace the medicament container.

Another drawback with many of the mentioned devices is that there is no feature or mechanism for handling the injection needle, neither automatic penetration nor automatic withdrawal.

WO 2013/153041 discloses an infusion device having a purely mechanical drive mechanism, including a mechanism for penetration and later withdrawal of the injection needle. Even though the device has proven advantages, especially the modular plunger rod and the injection speed control, it contains a large number of components that need to interact with each other in order to create the desired functionality.

In view of the above, there is still room for improvements regarding this type of medicament delivery device.

BRIEF DESCRIPTION OF INVENTION

The aim of the present invention is to remedy the drawbacks with the state of the art devices. This aim is obtained by a medicament delivery device having the features of the independent patent claim. Preferable embodiments of the invention form the subject of the dependent patent claims.

A medicament delivery device according to the invention may comprise a housing provided with a medicament delivery member assembly configured to be moved in relation to the housing from an initial position to a penetration position and from the penetration position back to the initial position.

In order to perform the movement of the medicament delivery member assembly, a penetration and withdrawal mechanism may be configured to control the movements of the medicament delivery member assembly. Further, an activation mechanism may be configured to interact with the penetration and withdrawal mechanism for initiating the movement of the medicament delivery member assembly from the initial position to the penetration position.

When a penetration and medicament delivery operation has been performed, a stop mechanism penetration and withdrawal mechanism may be arranged for initiating the movement of the medicament delivery member assembly from the penetration position back to the initial position.

According to a favourable solution, the penetration and withdrawal mechanism may comprise a driver operably connected to the medicament delivery member assembly and to the activation and stop mechanisms, wherein it may further comprise a drive element operably connected to the driver, a biased force element connected to the drive element and a switching element arranged between the driver and the drive element.

The operation of said activation mechanism may then allow the biased force element to interact with the drive element, causing a movement of the switching element such that the driver is moved towards a predetermined direction and slaves the medicament delivery member assembly to the penetration position; and wherein operation of said stop mechanism allows the biased force element, to further interact with the drive element, causing movement of the switching element such that the driver is moved in an opposite direction and slaves the medicament delivery member assembly back to the initial position.

With this design, the force element is used both for positioning the medicament delivery member holder both from the initial position to the penetration position and then from the penetration position to the initial position, wherein the force element interacts with both the drive element and the driver. This reduces the number of components and/or reduces the complexity of the medicament delivery device.

According to one aspect, the driver may comprise a rotator sleeve operably connected to the medicament delivery member holder and to the drive element such that pulling of the drive element will cause rotation of the rotator sleeve, in turn slaving the medicament delivery member holder, causing a linear movement of the medicament delivery member holder.

The drive element may comprise a flexible, non-elastic, band wound around rotator sleeve, and in that respect, the switching element may comprise a releasable element arranged to alter the winding direction of the drive element around the rotator sleeve. The flexible, non-elastic band is in this context to be defined as a band that can be bent to form curves around objects, but that does not extend elastically in any major way in the longitudinal or pulling direction.

According to a favourable solution, the switching element may be released when the medicament delivery member holder has reached the penetration position. The medicament delivery device is then ready when the stop mechanism penetration and withdrawal mechanism is later activated.

The switching element may comprise a pin that is releasibly attached to the rotator sleeve, wherein the drive element is wound around the pin in order to change the winding direction 180 degrees around the rotator sleeve. When the pin is removed, then the winding direction, and thus the pulling and rotational direction are altered.

The activation mechanism may preferably comprise a locking element arranged to lock the rotator sleeve in the initial position and in regard to that the activation mechanism may comprise a manually operable start button, operably arranged to act on the locking element for releasing the rotator sleeve.

Further, the stop mechanism may comprise a locking element arranged to lock rotator sleeve in the penetration position and in regard to that, the stop mechanism may comprise a manually operable stop button, operably arranged to act on the locking element for releasing the rotator sleeve.

According to another preferable solution, the medicament delivery device may further comprise an electrical drive unit, capable upon activation, to expel a dose of medicament from a medicament container arranged in the medicament delivery device. Preferably, the drive unit is activated by said activation mechanism and is deactivated by said stop mechanism.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

FIG. 5 is a detailed view of components comprised in the medicament delivery device of FIG. 1.

FIG. 6 is a detailed view of components comprised in the medicament delivery device of FIG. 1.

FIG. 7 is a detailed view of components comprised in the medicament delivery device of FIG. 1.

FIG. 8 is a detailed view of components comprised in the medicament delivery device of FIG. 1.

FIG. 9 is a detailed view of components comprised in the medicament delivery device of FIG. 1.

FIG. 11 is a detailed view of components comprised in the medicament delivery device of FIG. 1.

DETAILED DESCRIPTION OF THE INVENTION

Figure 1:
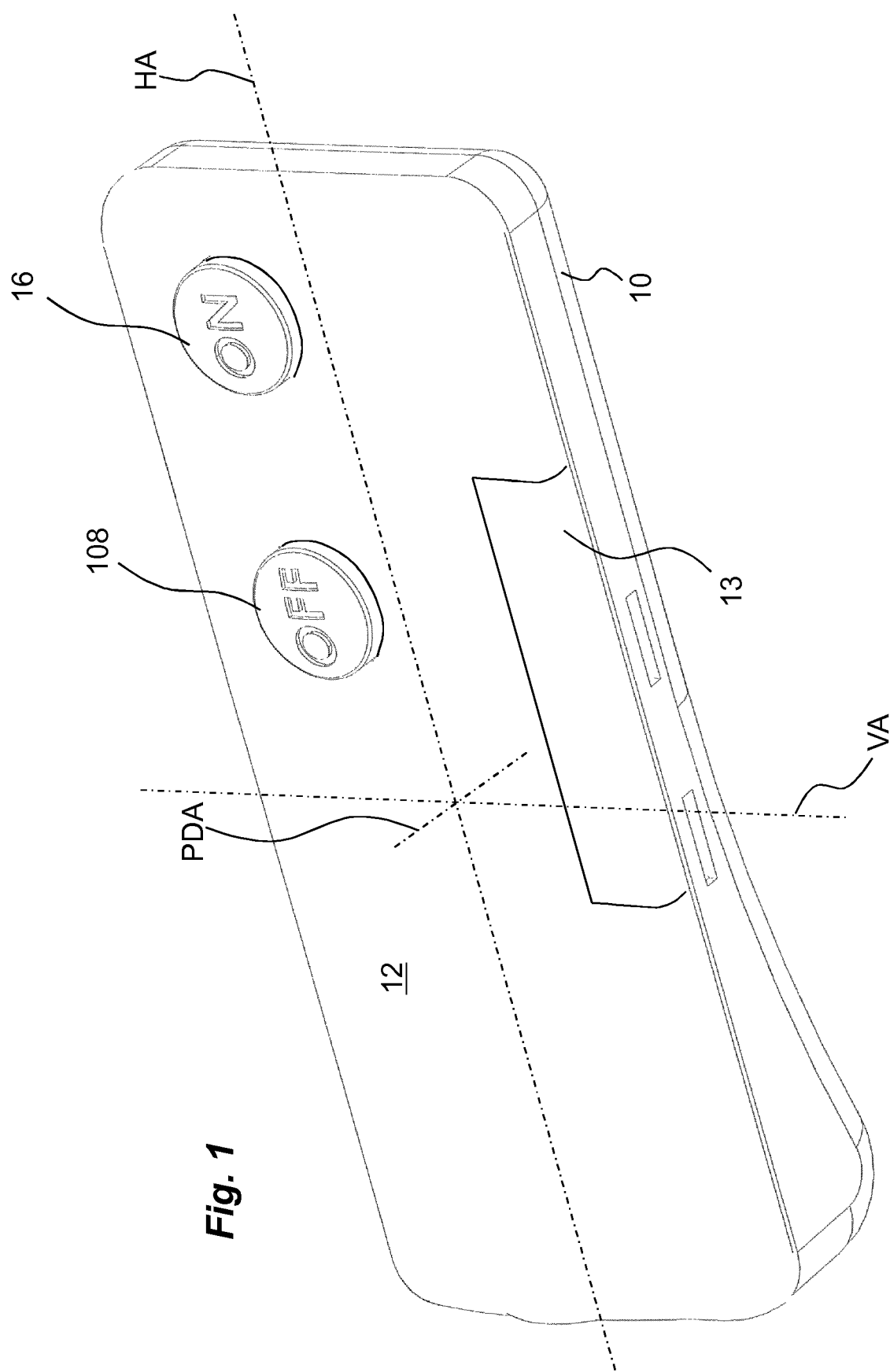
FIG. 1 is a perspective view of a medicament delivery device according to the invention.

The exemplary embodiment shown in the drawings comprises a proximal housing part 10 and a distal housing part 12, FIG. 1. It is however to be understood that the device can comprise further housing parts depending on design and production issues. The housing parts are arranged to accommodate a number of elements and mechanisms as will be described. Preferably, the assembled housing has a generally flat, rectangular shape having a measure or thickness, viewed along a proximal-distal axis, PDA, that is much less than the dimensions in the other two directions, vertical axis VA and horizontal axis HA. The distal housing part 12 is preferably arranged with a lid 13 for access to the interior of the medicament delivery device.

An activation mechanism 14 is arranged in the device for activating different functions of the device as will be described, see FIG. 2. The activation mechanism 14 comprises a push button 16, FIGS. 1 to 3, i.e. a start button, extending through a passage of the distal housing part 12. The start button 16 comprises a generally tubular body 20 provided with an end wall 22, FIG. 3, which acts as contact surface for a user as will be described. The end wall 22 of the start button 16 may be arranged with indicia that provide the user with information regarding its function, such as the word ON, indicating to a user that this is the button that activates the device. A centrally positioned shaft 24 is arranged on the end wall, extending in the proximal direction. The shaft 24 is arranged to fit into a generally tubular guide post 26 in the proximal housing part 10, FIG. 4.

Figure 3:
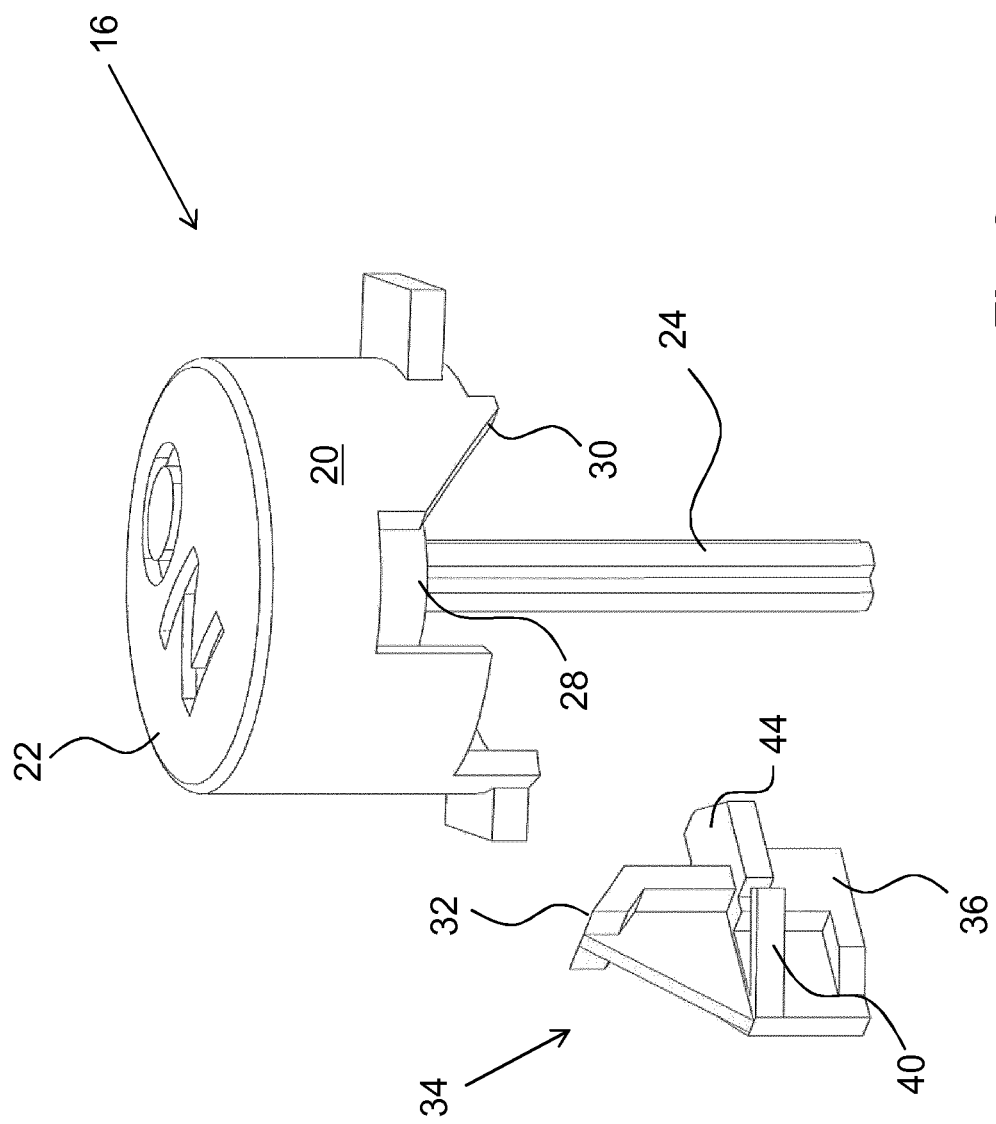
FIG. 3 is a detailed view of components comprised in the medicament delivery device of FIG. 1.
Figure 4:
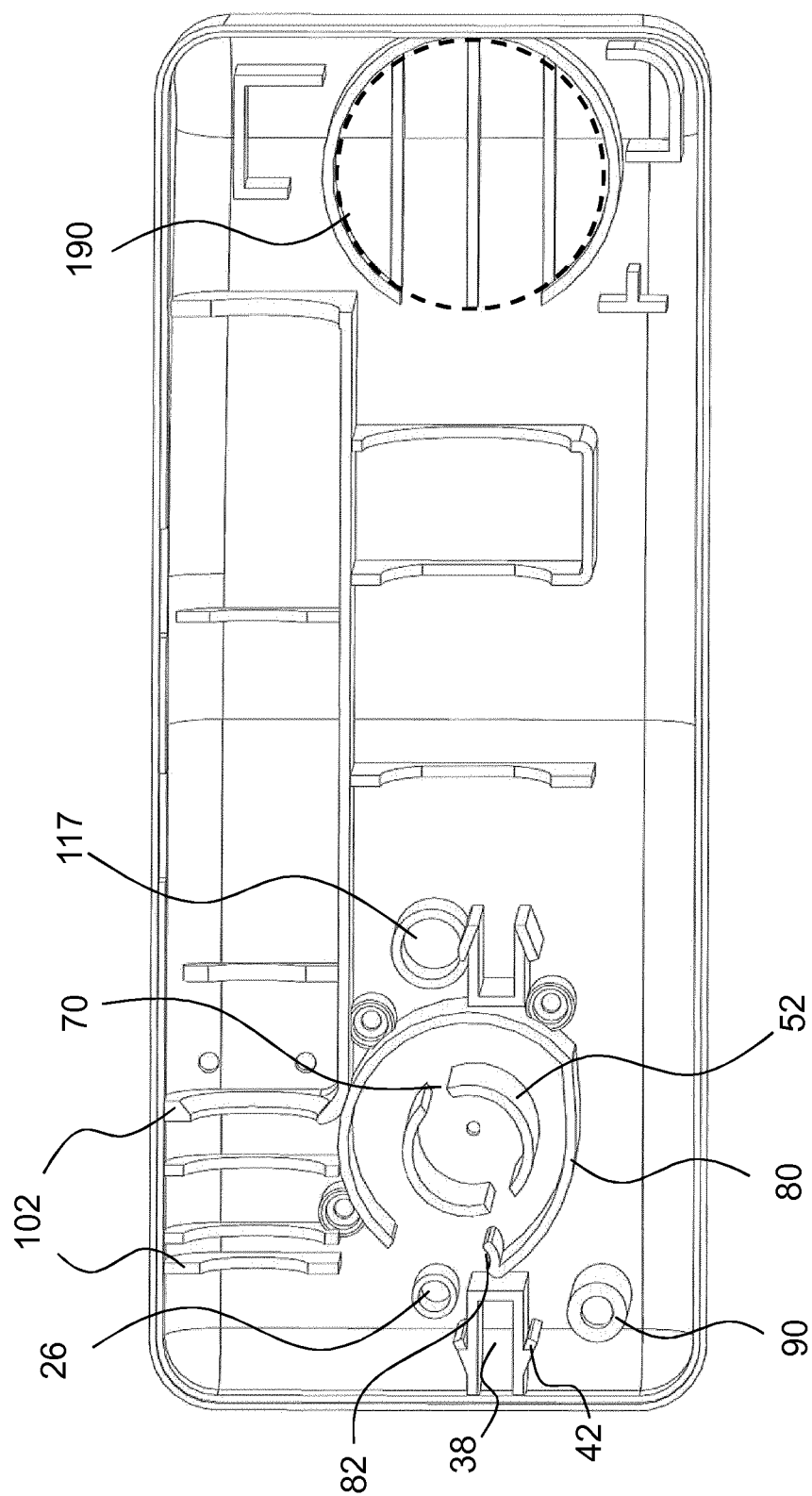
FIG. 4 is a detailed view of components comprised in the medicament delivery device of FIG. 1.

The body 20 of the start button 16 is further arranged with a cut-out 28, FIG. 3. One side surface 30 of the cut-out is arranged with an inclination, which inclination is intended to act on an inclined surface 32 of a start locking element 34 of the activation mechanism 14. The start locking element 34 is provided with a downwardly directed seat portion 36 that is designed to fit into a corresponding post 38, FIG. 4, arranged on the inner surface of the distal housing part 10. Further the start locking element 34 is arranged with flexible, inclined, arms 40 that are to interact with posts 42 arranged at the edge of the post 38 of the distal housing part 10. The start locking element 34 is further arranged with a protrusion 44 provided with side surfaces. The protrusion 44 is arranged to interact with a corresponding protrusion 46 on a driver that in the embodiment shown is designed as a generally tubular rotator sleeve 48, FIG. 5, comprised in a penetration and withdrawal mechanism. The protrusion 46 on the rotator sleeve 48 is attached to a generally radially outwardly extending tongue 50. The rotator sleeve 48 is journalled on a generally tubular post 52 arranged on the inner surface of the proximal housing part, FIG. 4. The rotator sleeve 48 is also arranged with two outwardly directed tongues 54, which are placed in line with each other as seen in the longitudinal direction of the rotator sleeve 48, FIG. 5a. Each tongue 54 is arranged with a generally semi-circular cut-out 56 as well as a hole or passage 58, the functions of which will be described below. The rotator sleeve 48 is further arranged with two spiral grooves 60 on its inner surface extending on opposite sides thereof.

Figure 2:
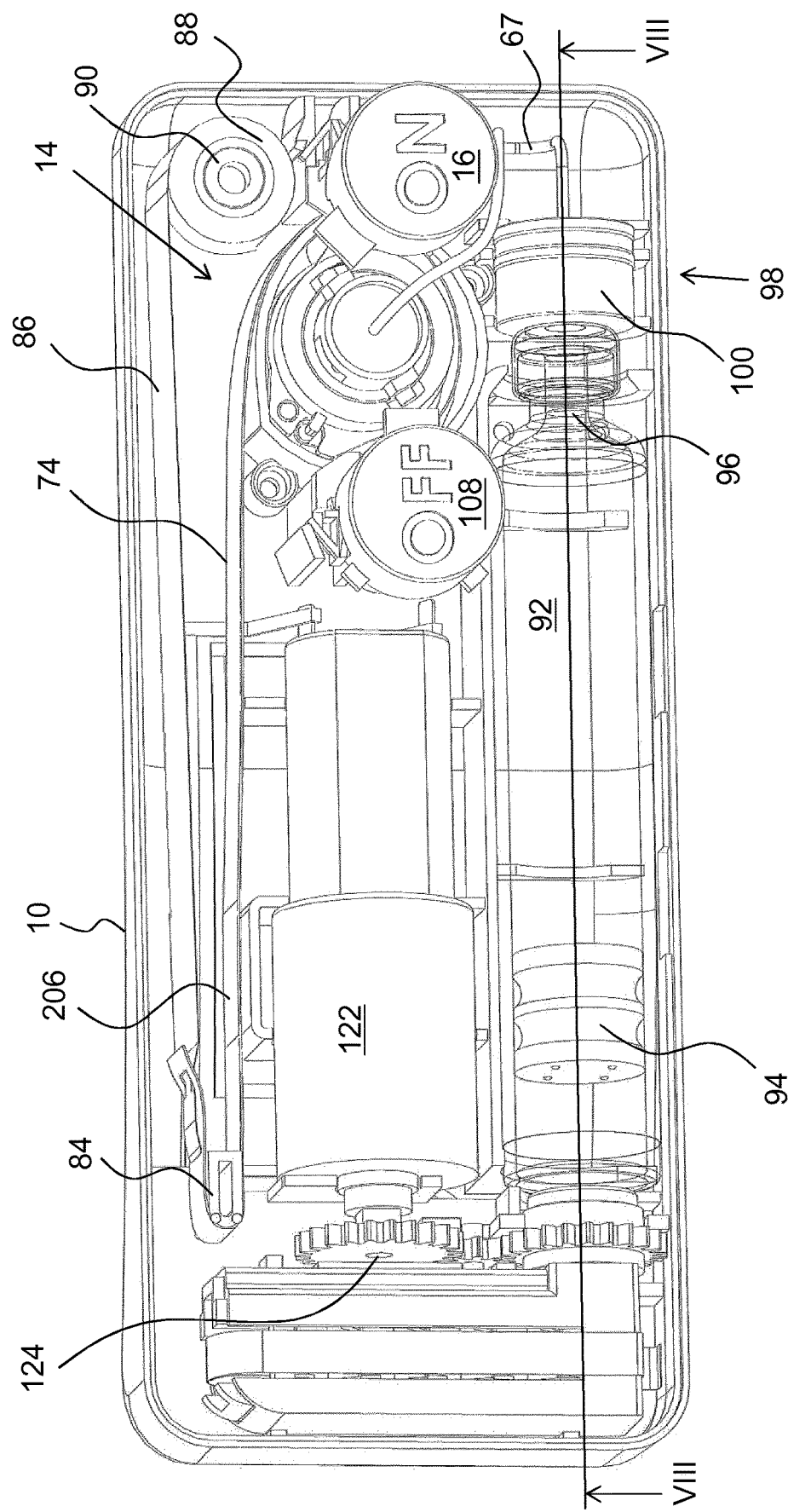
FIG. 2 is a perspective view of the medicament delivery device of FIG. 1 with a housing part removed.

A medicament delivery member assembly is further arranged, comprising a medicament delivery member holder 62 of a generally tubular shape is arranged in the post 52, FIG. 2, of the proximal housing part 10. The medicament delivery member holder 62 has a central transversal wall 64 to which a medicament delivery member 66 is attached, having a pointed penetration end and a connection end for a conduit 67 for medicament, FIG. 2. The medicament delivery member holder 62 is arranged with outwardly extending, generally rectangular protrusions 68 on opposite sides. These rectangular protrusions 68 are arranged to fit into longitudinally extending grooves 70 in the post 52, FIG. 4, thereby allowing linear movement of the medicament delivery member holder 62, but providing a rotational lock. Radially outside the rectangular protrusions 68, generally cylindrical protrusions 72 are arranged, which cylindrical protrusions 72 are intended to fit into the spiral grooves 60 of the rotator sleeve 48.

Further, a thin band-shaped element 74, a drive element, comprised in the penetration and withdrawal mechanism, FIG. 6, is connected to the rotator sleeve 48 with an end piece that is bent around a first attachment pin 76, FIG. 7, which first attachment pin 76 extends through the holes 58 of the tongues 54 of the rotator sleeve 48. As seen in FIG. 7b, the drive element 74 is then wound around the outer surface of the rotator sleeve 48 in a clockwise direction almost 360 degrees. It is then wound 180 degrees around a second attachment pin 78, also comprised in the penetration and withdrawal mechanism, which second attachment pin 78 is placed in the semi-circular cut-outs 56 of the tongues 54 of the rotator sleeve 48. The drive element 74 is then fed anti-clockwise around the rotator sleeve 48 and then outside a generally arc-shaped support wall 80, FIG. 4. An edge of the support wall 80 is arranged with a seat 82, into which seat 82 the second attachment pin 78 will be placed as described below.

The drive element 74 then extends along the inner of the proximal housing part up to a post 84, FIG. 2, provided with a rounded support surface, around which the drive element 74 is wound. The free end of the drive element 74 is then attached to a force element in the form of a clock spring 86, FIGS. 2 and 6, also comprised in the penetration and withdrawal mechanism. The force element 86 is wound around a generally cylindrical spring hub 88 with an inner end attached to the spring hub 88, which in turn is journalled on a post 90 fixed in the proximal housing part 10.

The proximal housing part 10 is further arranged to accommodate a medicament container 92, FIG. 2. In the preferred embodiment, the medicament container 92 comprises a generally tubular body with a first end arranged with a passage. Inside the passage a generally resilient stopper 94 is arranged, closing the passage, which stopper 94 is movable inside the body. The opposite second end of the body is preferably arranged with a neck portion 96, having a central opening. The opening of the neck portion 96 is sealed by a membrane or septum 97 of a pierceable material, FIG. 8. In the vicinity of the neck portion 96 of the medicament container 92, a piercing element 98 is arranged. The piercing element 98 comprises a generally tubular body 100, FIGS. 2, 8, arranged fixed to the proximal housing part between support walls 102, FIG. 4, and having an inner diameter somewhat larger than the diameter of the neck portion 96 of the medicament container 92. The body 100 of the piercing element 98 is arranged with a central wall 104, FIG. 8. A hollow piercing needle 106 is attached to the centre of the central wall 104. The piercing needle 106 is connected to the conduit 67 that runs to the medicament delivery member 66.

Further a stop button 108 is arranged to the device. It comprises a button with the same design as the start button, FIG. 9. It is arranged to interact with a stop locking element stop 110 having the same function and design as the locking element interacting with the start button. Thus the stop button 108 is arranged with an inclined surface 112 arranged to interact with an inclined surface 114 of the stop locking element 110. The button is arranged with a shaft 116 fitting in a post 117 of the distal housing part 10. Further, the stop locking element 110 of the stop button 108 is arranged with a protrusion 118 that is designed to inter-engage with the protrusion 46 on the rotator sleeve 48 in a manner that will be described below. The stop button 108 extends through a passage in the distal housing part 12 adjacent the passage of the start button, FIG. 1. The stop button 108 may also be arranged with indicia that provide the user with information regarding its function, such as the word OFF, indicating to a user that this is the button that de-activates the device.

Figure 10A:
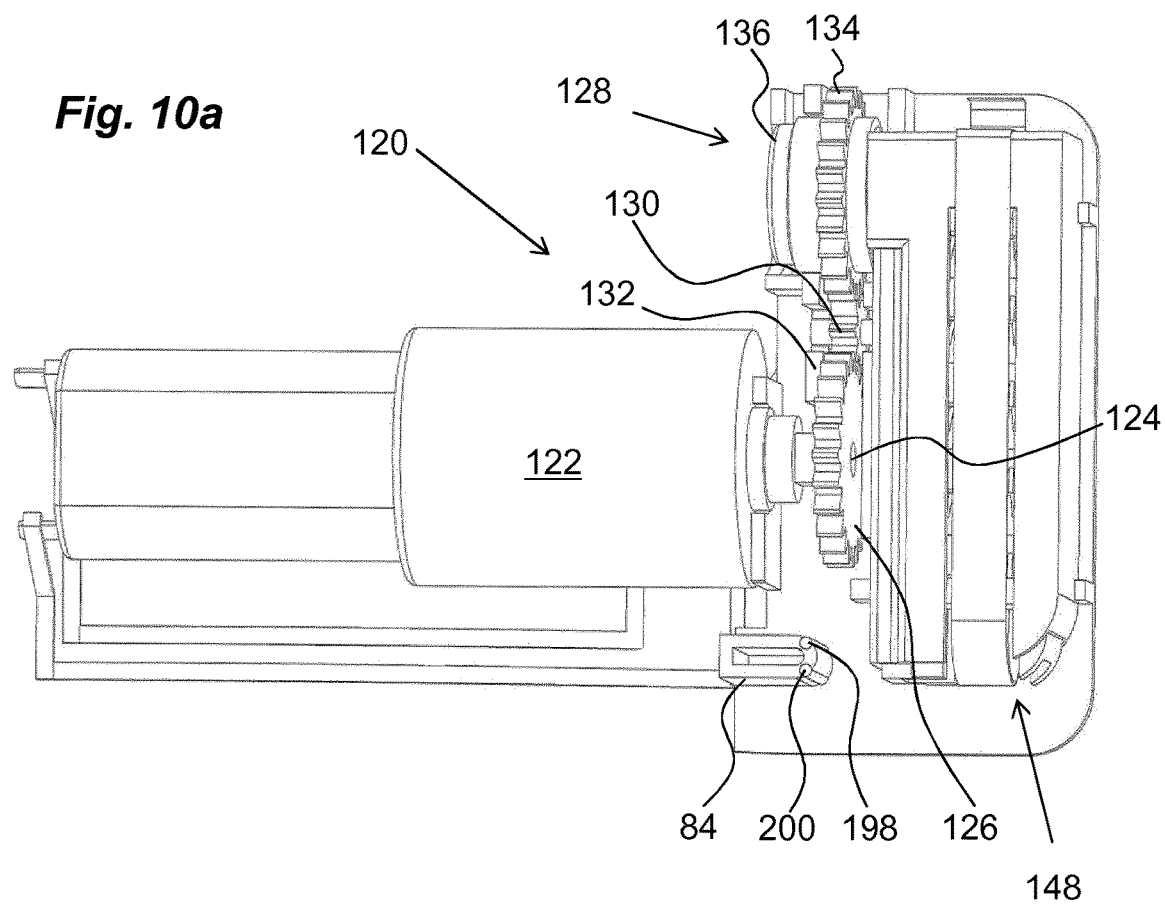
FIG. 10 is a detailed view of components comprised in the medicament delivery device of FIG. 1.

The device further comprises a drive unit 120, FIG. 10. The drive unit 120 comprises an electric motor 122 placed inside the housing and held in place by support surfaces of the proximal housing part 10. The electric motor 122 is arranged with a drive shaft 124. A first cog wheel 126 of a transmission 128 is attached to the drive shaft 124. The first cog wheel 126 is in engagement with a second cog wheel 130 of the transmission 128, where the second cog wheel 130 is journalled in seats 132 in the proximal housing part 10. The second cog wheel 130 is in engagement with circumferentially arranged teeth 134 of a generally ring-shaped plunger rod drive wheel 136, FIG. 11. The inner surface of the plunger rod drive wheel 136 is arranged with threads 138, FIG. 11. These threads 138 are in turn arranged to be in engagement with thread segments 140 of a first plunger rod element 142. The first plunger rod element 142 has a generally rectangular shape as seen in a cross-sectional view, where the thread segments 140 are arranged in the corners of the first plunger rod element 142, as seen in FIG. 11. The proximal end of the first plunger rod element 142 is directed towards the first end of the medicament container 92, wherein the proximal end of the first plunger rod element 142 is intended to be moved in contact with the stopper 94, as will be described below. The dimensions of the first plunger rod element 142 are such that it will fit into the tubular body of the medicament container 92.

The first plunger rod element 142 is arranged with two elongated grooves 144 on opposite sides thereof. These grooves 144 are intended to cooperate with guide beams 146 arranged extending from a plunger rod element holder 148. The guide beams 146 are arranged on opposite sides of a passage 150 in the plunger rod element holder 148, and the first plunger rod element 142 extends through the passage 150 in an initial position. The guide beams 146 are designed such that they have complementary shapes to, and fit into, the elongated grooves 144 of the first plunger rod element 142. Radially outwardly directed surfaces of the guide beams 146 are designed with a curved shape so as to act as support surfaces for the plunger rod drive wheel 136.

Figure 12A:
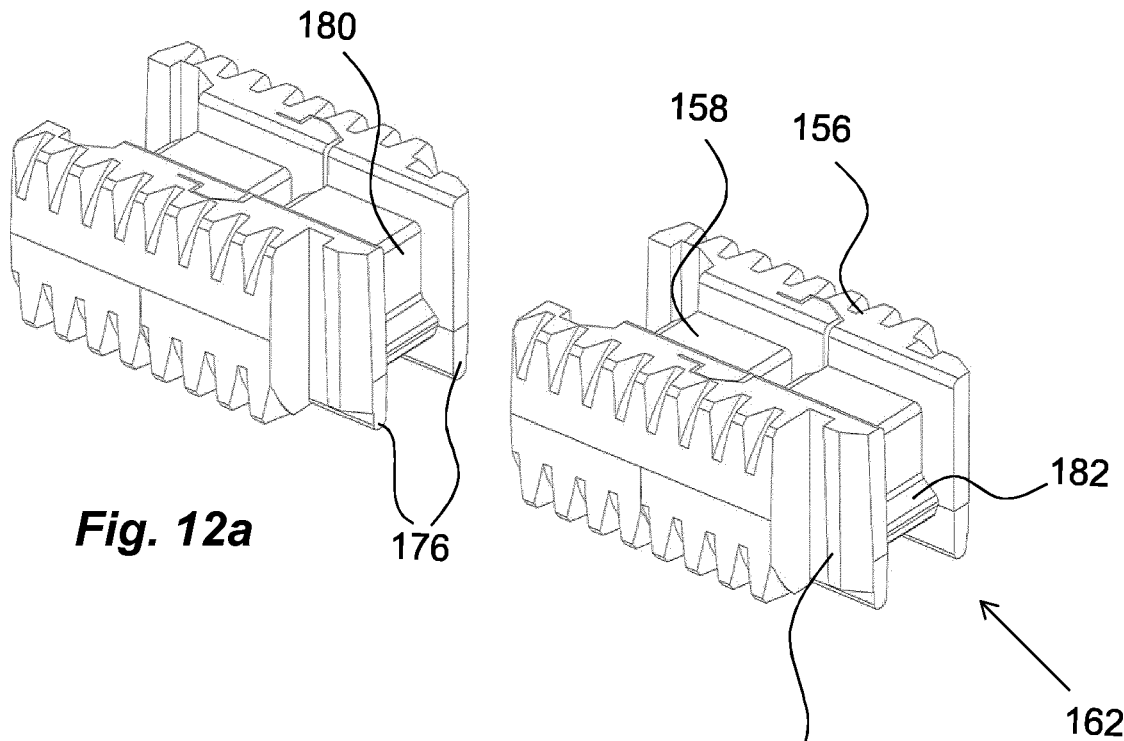
FIG. 12 is a detailed view of components comprised in the medicament delivery device of FIG. 1.
Figure 12B:
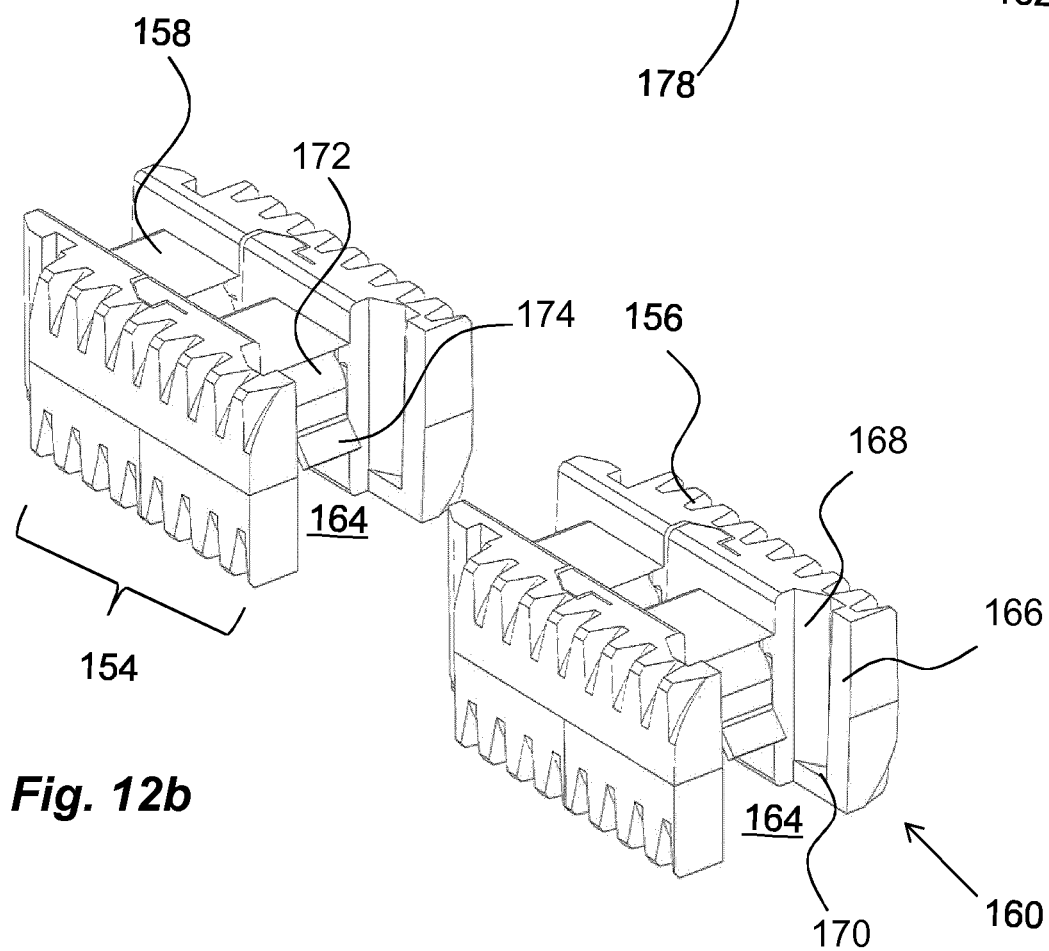

The plunger rod element holder 148 is further arranged with a generally rectangularly shaped storage compartment 152, which storage compartment 152 has four side walls and extends generally perpendicularly to the passage 150. In the storage compartment 152, a number of further plunger rod elements 154 are placed. The further plunger rod elements 154 have a shape generally corresponding to the first plunger rod element 142 as seen in FIG. 12, i.e. having a generally rectangular cross-sectional shape, where the corners are provided with thread segments 156, and with longitudinal grooves 158. The further plunger rod elements 154 are arranged with first 160 and second 162 connection elements at their ends, where the first plunger rod element 142 is arranged with a first connection element 160 at its distal end. The first connection element 160 comprises a transversally arranged groove 164. The side edges of the groove 164 are arranged with inwardly directed ledges 166, where the groove 164 and each ledge 166 form a slit 168. Stop surfaces 170 are arranged at a lower end of the slits 168 as seen in FIG. 12b. A flexible tongue 172 is arranged in the groove 164, having a certain inclination as well as a wedge-shaped end protrusion 174.

A further plunger rod element 154 that is placed adjacent the first plunger rod element 142 is arranged with a second connection element 162 at its end facing towards the first plunger rod element 142. The second connection element 162 comprises two proximally directed ledges 176, designed with a distance between them, generally corresponding to the width of the groove 164 of the first connection element 160. At the free ends of the ledges 176 outwardly extending protrusions 178 are arranged, which protrusions 178 have a cross-sectional shape complementary to the shape of the slits 168 such that the protrusions 178 can slide into the slits 168 when a further plunger rod element 154 is moved in a direction transversal to the longitudinal direction of the plunger rod elements, as will be described.

Further, an end surface 180 of the further plunger rod element 154 between the protrusions 178 is arranged with an attachment member 182, with which the flexible tongue 172 with its wedge-shaped end protrusion 174 may engage when the plunger rod elements are connected as described. All further plunger rod elements 154 in the storage compartment 152 are arranged with the mentioned first and second connection elements 160, 162 so as to create an elongated plunger rod by the interconnected plunger rod elements. The plunger rod elements in the compartment are urged towards the passage 150 by an end piece 184, FIG. 11, placed at the top of the stack of further plunger rod elements 154 in the storage compartment 152. The end piece 184 is tensioned by a generally flat spring element 186 with one end seated in the end piece 184 and the opposite end in contact with the bottom surface 188 of the plunger rod element holder 148.

Figure 10B:
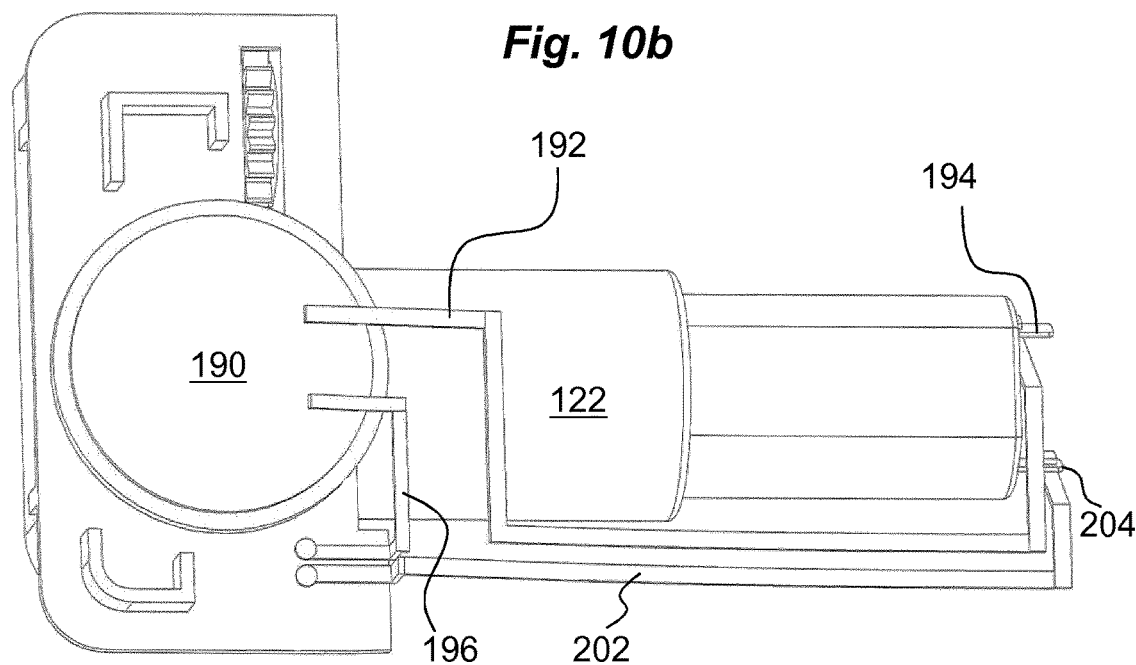

The device is further arranged with a suitable power source 190, FIG. 10b, that in the embodiment shown is a battery of a generally flat and circular shape, a so called button cell. It is however to be understood that other types of power sources are feasible within the scope of the invention. For instance if the force requirement is large, then larger batteries may be needed. The poles of the battery are connected to leads where a first lead 192 is connected to a first input connector 194 of the electric motor 122. A second lead 196 runs from the battery 190 to a first contact surface 198, FIG. 10a, arranged on a side surface of the post 84. A second contact surface 200 is arranged on the side surface of the post 84 with a distance to the first contact surface 198. A third lead 202 runs from the second contact surface to a second input connector 204 of the electric motor 122. Further the drive element 74 is arranged with a conductive surface 206, FIG. 2, the function of which will be explained below.

Figure 13:
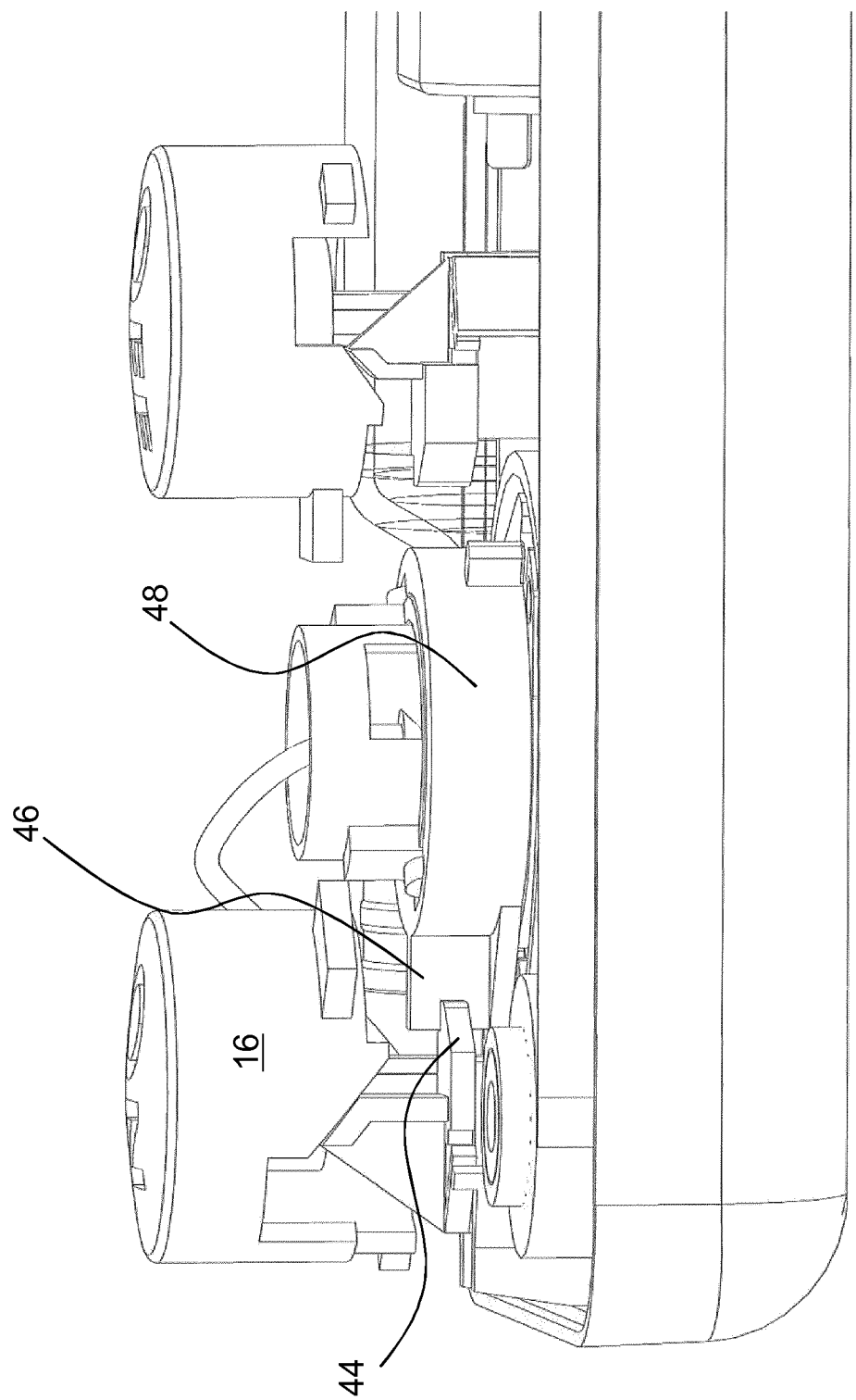
FIG. 13 is a detailed view of a functional state of the medicament delivery device of FIG. 1.

The device is intended to function as follows. When delivered to a user, it is energized in that the force element 86 is tensioned and held in that state by the drive element 74 wound around the rotator sleeve as seen in FIG. 7a, wherein the rotator sleeve 48 is held against rotating by the protrusion 44 of the start locking element 34 of the start button 16 engaging the protrusion 46 of the rotator sleeve 48 as seen in FIG. 13.

When the device is to be used the lid 13 on the distal housing part 12 is opened and a medicament container 92 is placed in the interior of the device, after which the lid 13 is closed. The device is then attached to the body of the patient with suitable elements. That could for example be an adhesive on the proximal surface of the proximal housing part 10, elastic straps around the body of the patient, for example.

Figure 14:
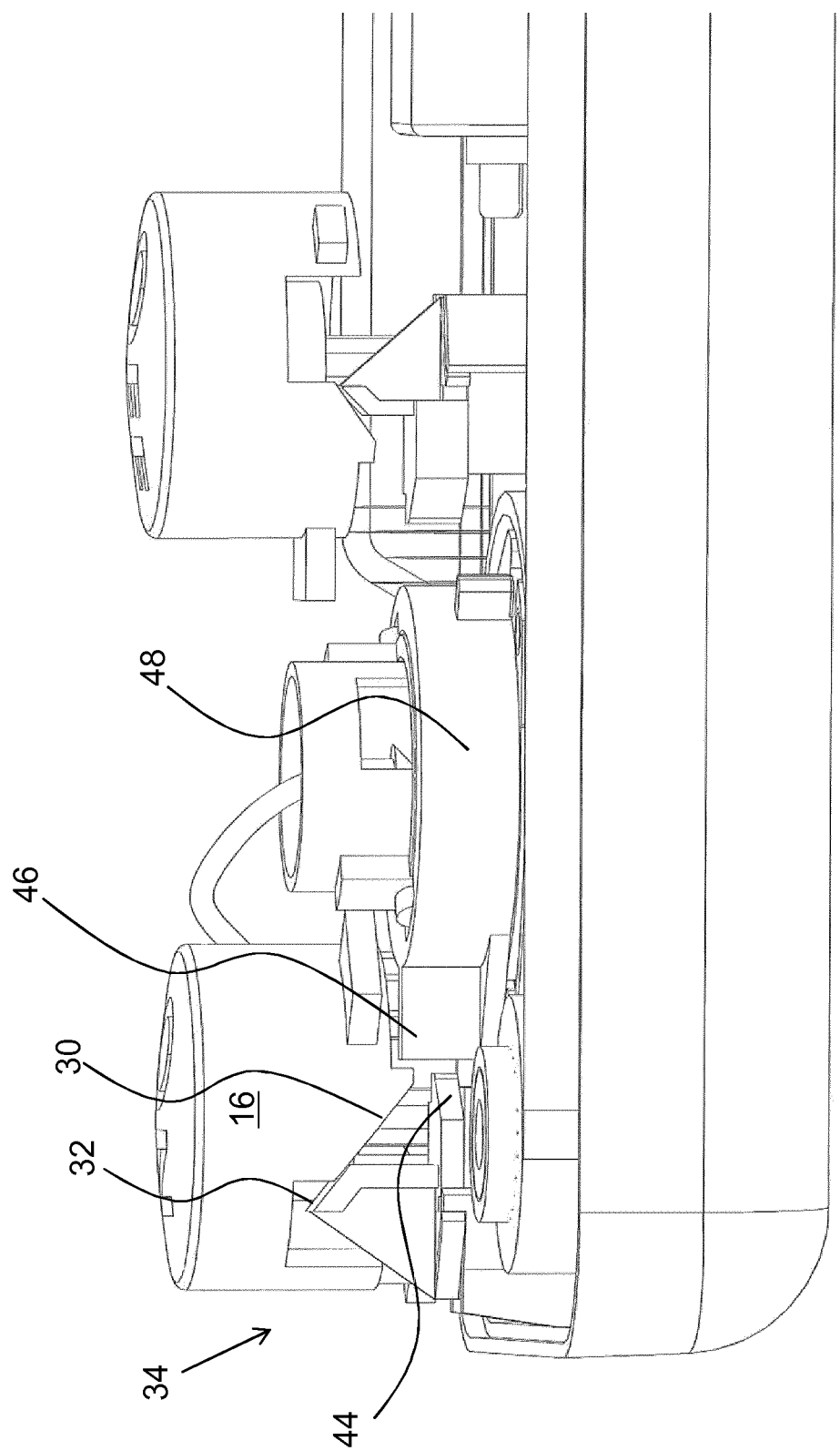
FIG. 14 is a detailed view of a functional state of the medicament delivery device of FIG. 1.
Figure 15:
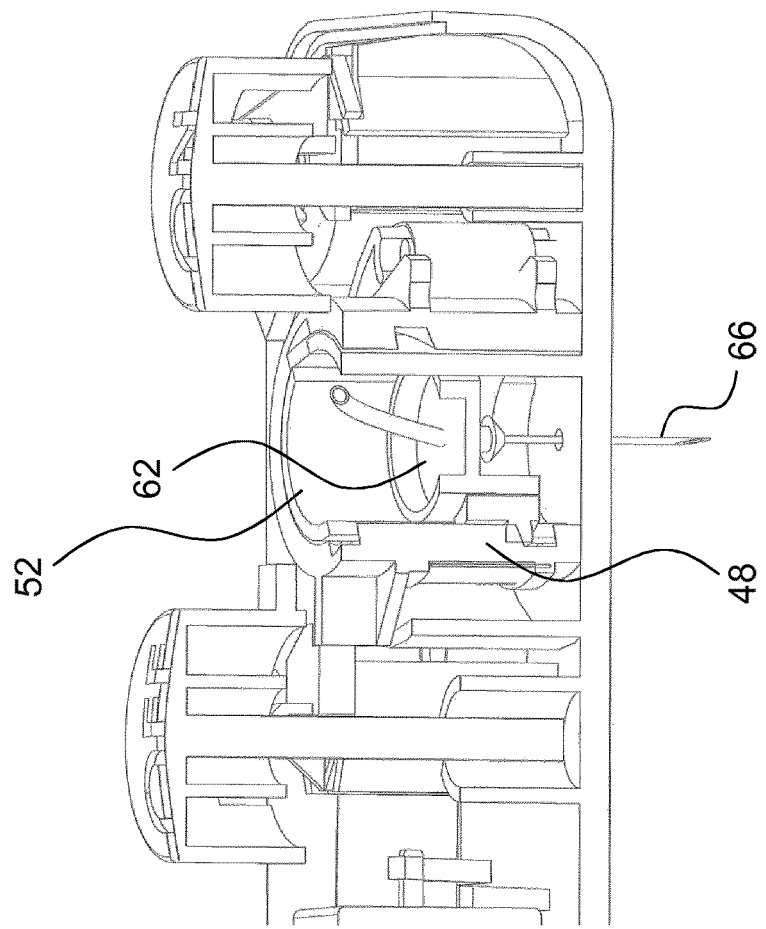
FIG. 15 is a detailed view of a functional state of the medicament delivery device of FIG. 1.

When a user is to administer a dose of medicament, the start button is depressed. This causes the inclined surface 30 of the start button 16 to act on the inclined surface 32 of the start locking element 34, whereby the start locking element 34 is moved away from the rotator sleeve 48. This movement causes the protrusion 44 of the start locking element to move out of engagement with the protrusion 46 of the rotator sleeve 48, thus releasing the rotator sleeve 48, FIG. 14. Because of the force from the force element 84 pulling on the drive element 74, and due to the drive element 74 being wound around the outer surface of the rotator sleeve 48, the rotator sleeve 48 will rotate around the post 52. Due to the connection between the rotator sleeve 48 and the medicament delivery member holder 62 with its cylindrical protrusions 72 placed in the spiral grooves 60 of the rotator sleeve 48 and due to the rectangular protrusions 68 of the medicament delivery member holder 62 being arranged in the grooves 70 of the post 52, rotation of the rotator sleeve 48 will cause the medicament delivery member holder 62 with the medicament delivery member 66 to move in the proximal direction, causing a penetration of the tissue of the user, FIG. 15.

Figure 16:
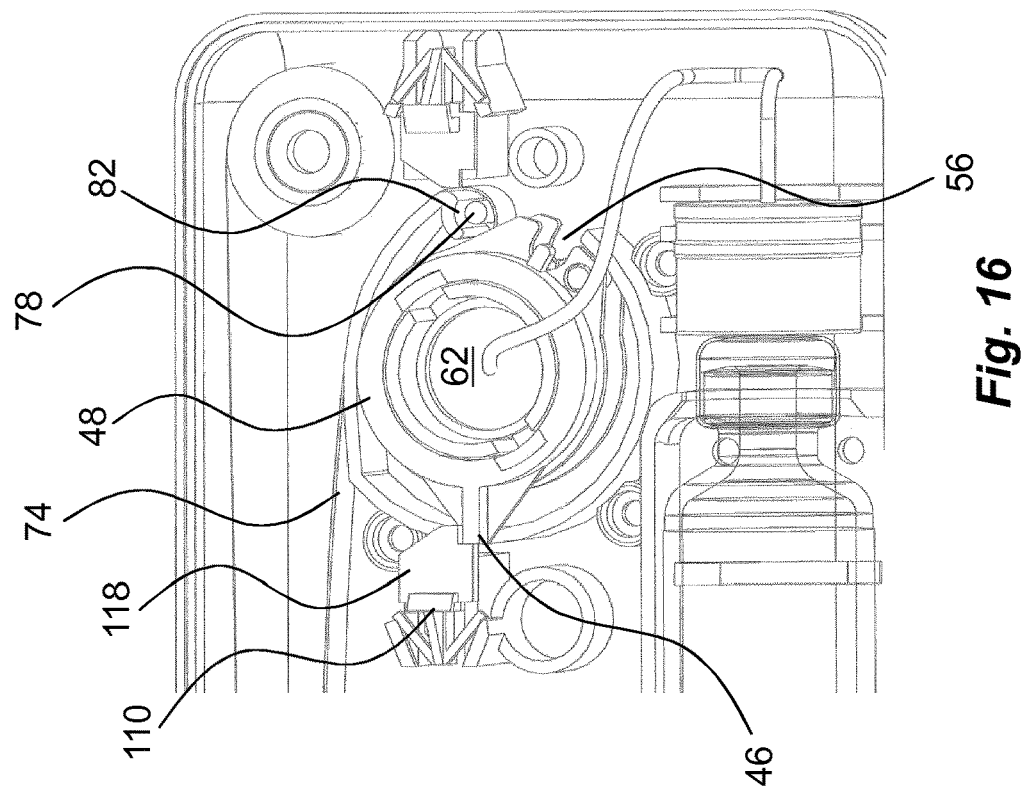
FIG. 16 is a detailed view of a functional state of the medicament delivery device of FIG. 1.

During rotation of the rotator sleeve 48, it will come to a rotational position where the second attachment pin 78 will be pulled out of the semi-circular cut-outs 56 and will reach the seat 82 at the edge of the support wall 80 and will be held there, whereby the rotation of the rotator sleeve 48 will stop due to that the drive element 74 now is wound in the opposite direction around the rotator sleeve. However, the rotator sleeve 48 is prevented from being rotated in the opposite direction because the tongue 50 of the rotator sleeve with the protrusion 46 will, during rotation, come in contact and pass the protrusion 118 of the stop locking element 110 of the stop button 108, FIG. 16. Thus, the rotator sleeve 48 is held stationary with the force element 86 still tensioned.

Figure 17:
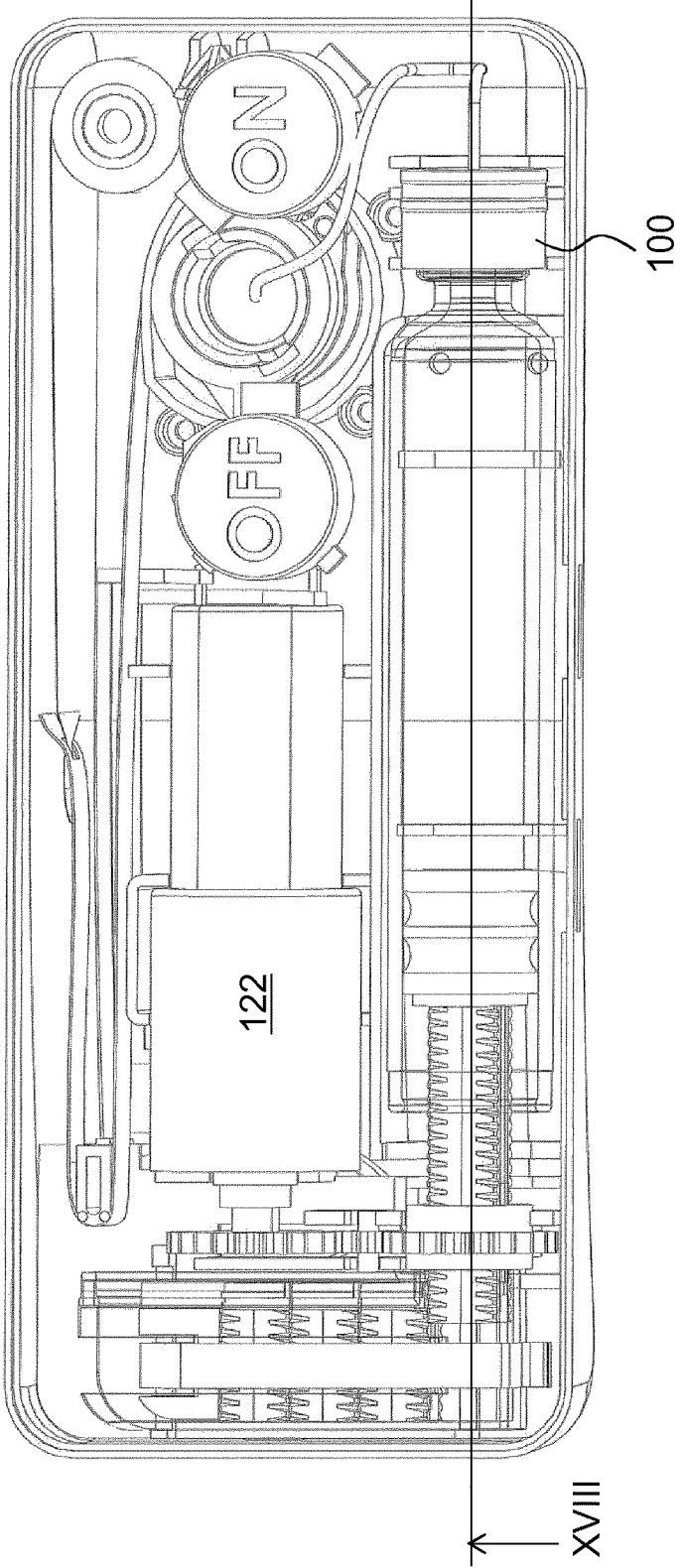
FIG. 17 is a detailed view of a functional state of the medicament delivery device of FIG. 1.
Figure 18:
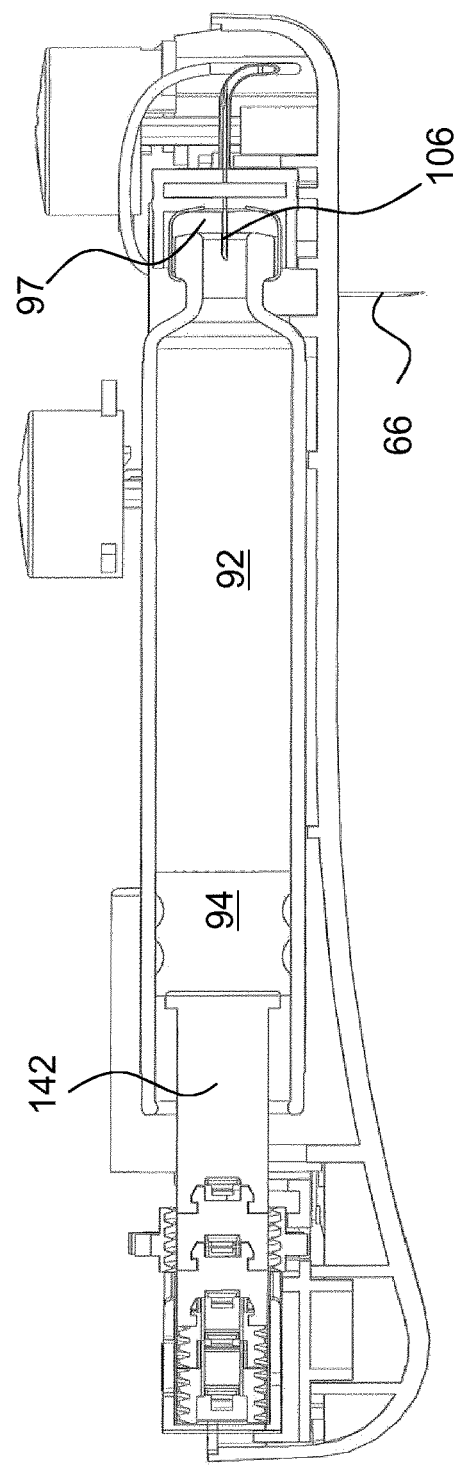
FIG. 18 is a detailed view of a functional state of the medicament delivery device of FIG. 1.

When the force element 86 is pulling the drive element 74, the drive element 74 will slide around the post 84. This will cause the conductive surface 206 to also be wound around the post 84 at the position where the second attachment pin is released and the rotation of the rotator sleeve stops. Now the conductive surface 206 is in contact with the two contact surfaces 198 and 200 whereby the electric circuit is closed and the electric motor 122 is activated and starts to rotate its drive shaft 124. Thus the first cogwheel 126 starts rotating and the rotation of the first cogwheel 126 is transmitted to the second cogwheel 130 of the transmission 128 and then to the plunger rod drive wheel 136 via its teeth 134. Since the threads 138 of the plunger rod drive wheel 136 are in contact with the thread segments 140 of the first plunger rod element 142, the first plunger rod element 142 is moved in the direction of the medicament container 92. When the proximal end of the first plunger rod element 142 comes in contact with the stopper 94, it will slide the medicament container 92 towards the piercing element 98 due to the incompressibility of the medicament inside the medicament container 92, FIGS. 17 and 18. The sliding of the medicament container 92 will cause the needle of the piercing element 98 to penetrate the septum 97 of the neck portion 96 of the medicament container 92, thereby creating a fluid passage between the medicament container 92 and the medicament delivery member 66, FIG. 18. Further movement of the first plunger rod element 142 will move the stopper 94 inside the medicament container 92 towards its neck portion 96, whereby medicament will be forced through the fluid connection and through the medicament delivery member 66, thereby delivering medicament to the user.

When the first plunger rod element 142 has moved a distance towards and inside the medicament container 92, the space behind the first plunger rod element 142 is so large that a further plunger rod element 154 may be pushed in the vertical direction by the flat band spring element 186 acting on the uppermost positioned end piece 184 in the storage compartment 152. When the following further plunger rod elements 154 are pushed downwards in the vertical direction, they are connected to a previous plunger rod element in that the protrusions 178 of the second connection elements 162 of the further plunger rod element 154 segment fit into the slits 168 of the groove 164 of the first connection element 160 and wherein the plunger rod elements are inter-locked by the flexible tongues 172 engaging the attachment members 182. In this manner a sequential "building" of a continuous plunger rod is performed with the segments while performing injection of medicament from the medicament container 92 through the medicament delivery member 66.

Figure 19:
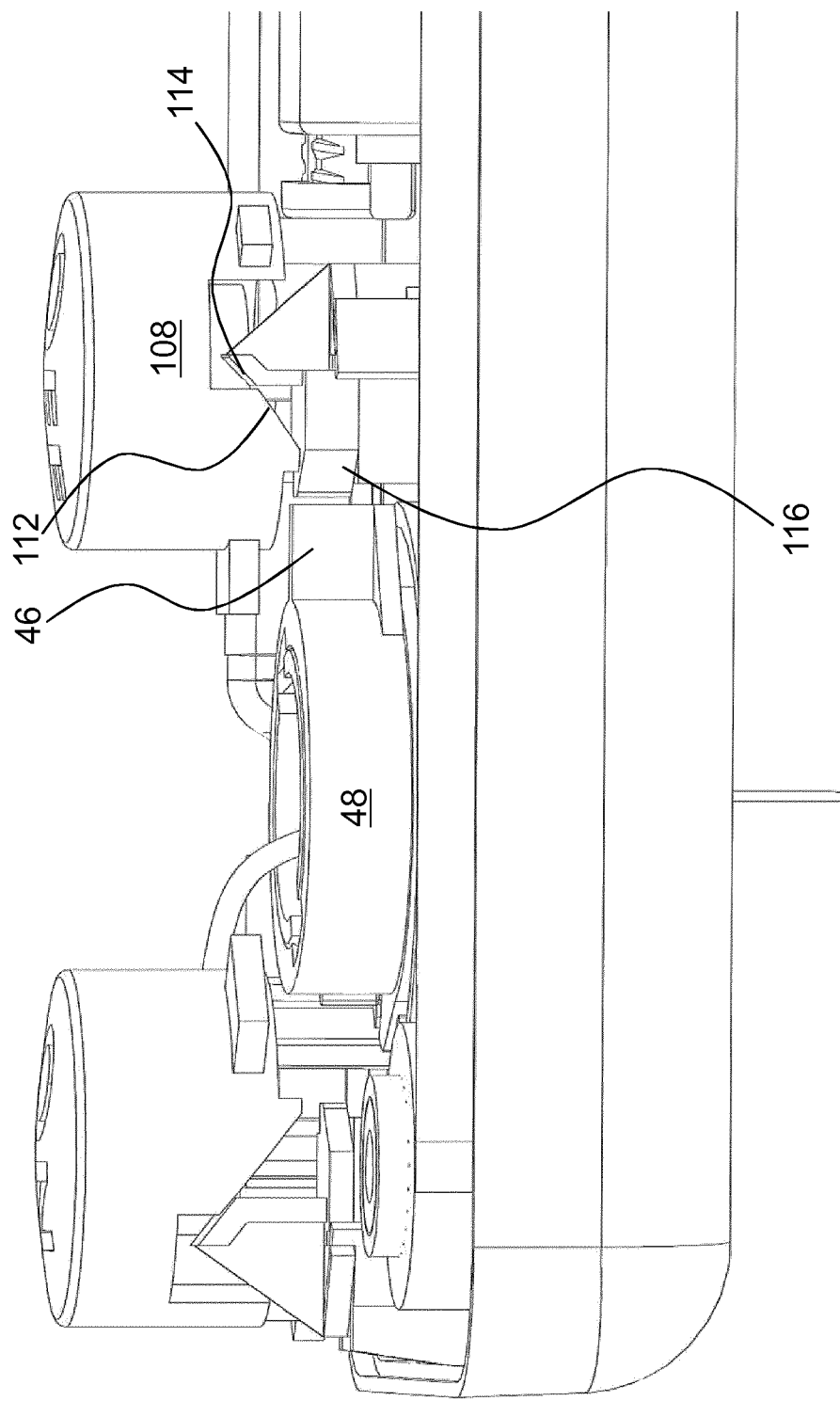
FIG. 19 is a detailed view of a functional state of the medicament delivery device of FIG. 1.
Figure 20:
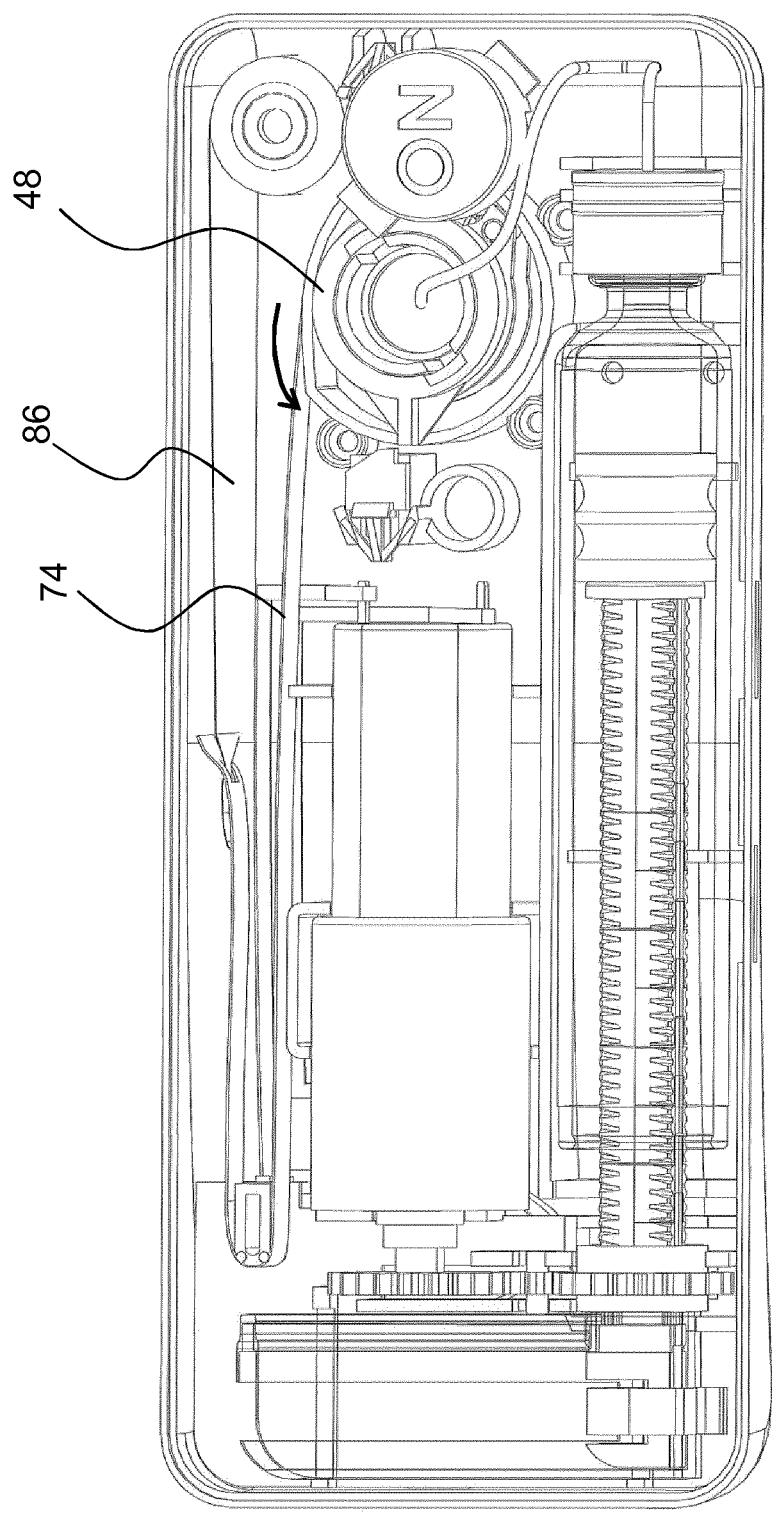
FIG. 20 is a detailed view of a functional state of the medicament delivery device of FIG. 1.
Figure 21:
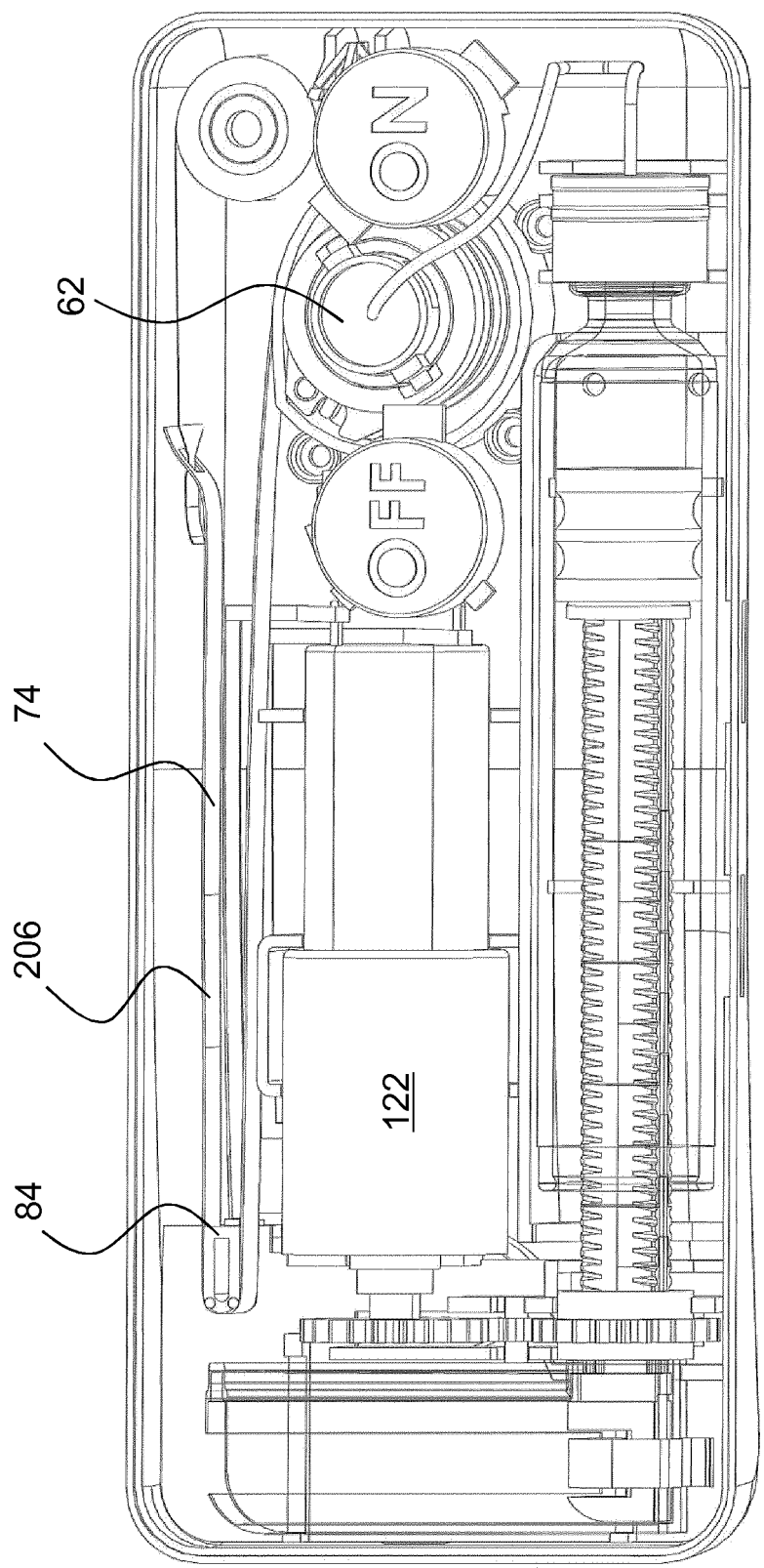
FIG. 21 is a detailed view of a functional state of the medicament delivery device of FIG. 1.

When the plunger rod has pushed the stopper 94 inside the medicament container 92 to the most proximal position, whereby the dose delivery sequence is ended, the device can be switched off. In order to do this the stop button 108 is depressed. The pushing of the stop button 108 causes its inclined surface 112 to act on the inclined surface 114 of the stop locking element 110 so that it is moved away from the protrusion 46 of the rotator sleeve 48 as seen in a radial direction, FIG. 19. This movement causes the protrusion 118 of the locking element to move out of contact with the protrusion 46 of the rotator sleeve 48, whereby the rotator sleeve 48 is released. Due to the remaining force of the force element 86, it will pull on the drive element 74, which in turn will cause the rotator sleeve 48 to rotate, however in the opposite direction due to the winding direction of the drive element 74 around the rotator sleeve 48, see arrow in FIG. 20. Because of the connection between the rotator sleeve 48 and the medicament delivery member holder 62, the spiral grooves 60 of the rotator sleeve 48 will cause the medicament delivery member holder 62 to move in the distal direction, causing a withdrawal of the medicament delivery member 66 from the body of the user. At the same time, the conductive surface 206 of the drive element 74 is moved from the contact surfaces of the post, FIG. 22, whereby the electric motor 122 is stopped. The medicament delivery device can now be removed from the body and recharged or discarded.

It is to be understood that the embodiment described above and shown in the drawings is to be regarded only as a non-limiting example of the invention and that it may be modified in many ways within the scope of the patent claims.

COMPONENT LIST 10 proximal housing part
12 distal housing part
13 lid
14 activation mechanism
16 start button
18 passage
20 tubular body
22 end wall
24 shaft
26 guide post
28 cut-out
30 side surface
32 inclined surface
34 start locking element
36 seat portion
38 post
40 flexible arm
42 post
44 protrusion
46 protrusion
48 driver, rotator sleeve
50 tongue
52 post
54 tongue
56 cut-out
58 hole
60 spiral groove
62 medicament delivery member holder
64 wall
66 medicament delivery member
67 conduit
68 rectangular protrusion
70 groove
72 cylindrical protrusion
74 drive element
76 first attachment pin
78 second attachment pin
80 support wall
82 seat
84 post
86 force element
88 spring hub
90 post
92 medicament container
94 stopper
96 neck portion
97 septum
98 piercing element
100 body
102 support wall
104 central wall
106 piercing needle
108 stop button
110 stop locking element
112 inclined surface
114 inclined surface
116 shaft
117 post
118 protrusion
120 drive unit
122 electric motor
124 drive shaft
126 first cog wheel
128 transmission
130 second cog wheel
132 seat
134 teeth
136 plunger rod drive wheel
138 threads 140 thread segment
142 first plunger rod element
144 groove
146 guide beam
148 plunger rod element holder
150 passage
152 storage compartment
154 further plunger rod element
156 thread segment
158 groove
160 first connection
162 second connection
164 groove
166 ledge
168 slit
170 stop surface
172 flexible tongue
174 wedge-shaped protrusion
176 ledge
178 protrusion
180 end surface
182 attachment member
184 end piece
186 spring element
188 bottom surface
190 power source, battery
192 first lead
194 first input connector
196 second lead
198 first contact surface
200 second contact surface
202 third lead
204 second input connector
206 conductive surface

The invention claimed is:

1. A medicament delivery device comprising:
   a housing;
   a medicament delivery member;
   a rotator sleeve configured to control movement of the medicament delivery member, wherein the medicament delivery member is arranged coaxially with the rotator sleeve;
   a first button;
   a second button;
   a drive element;
   a biased force element; and
   a switching element,
   wherein operation of the first button is configured to cause the biased force element to interact with the drive element, causing movement of the switching element such that the rotator sleeve is moved in a first rotational direction to move the medicament delivery member coaxially with respect to the rotator sleeve to a penetration position from an initial position; and wherein operation of the second button is configured to cause the biased force element to further interact with the drive element, causing movement of the switching element such that the rotator sleeve is moved in a second rotational direction that is opposite the first rotational direction to move the medicament delivery member coaxially with respect to the rotator sleeve back to the initial position.

2. The medicament delivery device according to claim 1, wherein the drive element comprises a flexible, non-elastic band wound around the rotator sleeve.

3. The medicament delivery device according to claim 1, wherein pulling of the drive element is configured to cause rotation of the rotator sleeve, in turn causing a linear movement of the medicament delivery member.

4. The medicament delivery device according to claim 1, wherein the rotator sleeve comprises a spiral-shaped groove.

5. The medicament delivery device according to claim 4, wherein the spiral-shaped groove is suitable for cooperating with protrusions on the medicament delivery member.

6. The medicament delivery device according to claim 1, wherein the housing comprises a tubular post provided with a groove.

7. The medicament delivery device according to claim 6, wherein the medicament delivery member is arranged to fit into the tubular post and is provided with protrusions fitting into the groove.

8. The medicament delivery device according to claim 1, wherein the switching element is releasably attached to the rotator sleeve.

9. The medicament delivery device according to claim 1, wherein the switching element is arranged to alter a winding direction of the drive element around the rotator sleeve.

10. The medicament delivery device according to claim 1, wherein the switching element is configured to detach from the rotator sleeve when the medicament delivery member has reached the penetration position.

11. The medicament delivery device according to claim 1, wherein the switching element comprises a pin.

12. The medicament delivery device according to claim 11, wherein the switching element further comprises a band that is wound around the pin and configured for reversing a winding direction of the drive element around the rotator sleeve.

13. The medicament delivery device according to claim 1, wherein the first button is configured to lock the rotator sleeve in a non-activated position.

14. The medicament delivery device according to claim 13, wherein the first button is manually operable release the rotator sleeve.

15. The medicament delivery device according to claim 1, wherein the second button is configured to lock the rotator sleeve in the penetration position.

16. The medicament delivery device according to claim 15, wherein the second button is arranged to release the rotator sleeve.

17. The medicament delivery device according to claim 1, further comprising
   an electrical drive unit configured upon activation to expel a dose of medicament from a medicament container arranged in the medicament delivery device.

18. The medicament delivery device according to claim 17, wherein the electrical drive unit is configured to be activated by the first button.

19. The medicament delivery device according to claim 17, wherein the electrical drive unit is configured to be deactivated by the second button.

20. The medicament delivery device according to claim 1, further comprising a medicament delivery member holder comprising a central transversal wall to which the medicament delivery member is attached, the medicament delivery member comprising a pointed penetration end and a connection end for a conduit for medicament.

21. The medicament delivery device according to claim 1,
wherein the rotator sleeve is operably connected to the medicament delivery member and to the drive element,
wherein said switching element is releasably attached to said rotator sleeve,
wherein said switching element is arranged to alter a winding direction of said drive element around said rotator sleeve, and
wherein said switching element is detached from said rotator sleeve when the medicament delivery member has reached said penetration position.

* * * * *